US008168224B2

(12) United States Patent
Xiaoping et al.

(10) Patent No.: US 8,168,224 B2
(45) Date of Patent: May 1, 2012

(54) SODIUM ALGINATE MICROSPHERE VASCULAR EMBOLUS CONTAINING WATER-SOLUBLE DRUG AND PREPARATION AND APPLICATION THEREOF

(75) Inventors: Li Xiaoping, Beijing (CN); Li Xinjian, Beijing (CN); Cui Heng, Beijing (CN); Wei Lihui, Beijing (CN); Feng Jie, Beijing (CN); Lang Jinghe, Beijing (CN); Xiang Yang, Beijing (CN); Lei Chengzhi, Beijing (CN); Hong Hong, Beijing (CN)

(73) Assignee: Beijing Shengyiyao Science & Technology Development Co., Ltd., Beijing (CN)

( * ) Notice: Subject to any disclaimer, the term of this patent is extended or adjusted under 35 U.S.C. 154(b) by 479 days.

(21) Appl. No.: 11/959,538

(22) Filed: Dec. 19, 2007

(65) Prior Publication Data
US 2009/0162440 A1    Jun. 25, 2009

(51) Int. Cl.
*A61K 9/14* (2006.01)
*A01N 59/22* (2006.01)
(52) U.S. Cl. ....................................... 424/489; 424/620
(58) Field of Classification Search .................. None
See application file for complete search history.

(56) References Cited

U.S. PATENT DOCUMENTS

| 5,776,486 A * | 7/1998 | Castor et al. ................ 424/450 |
| 2004/0091543 A1 * | 5/2004 | Bell et al. ...................... 424/489 |
| 2004/0096662 A1 * | 5/2004 | Lanphere et al. ............. 428/402 |
| 2005/0196464 A1 * | 9/2005 | Hu et al. ........................ 424/623 |
| 2008/0020052 A1 * | 1/2008 | Li et al. .......................... 424/490 |

FOREIGN PATENT DOCUMENTS

WO    WO 2006013309 A1 *    2/2006
WO    WO 2006029554 A1 *    3/2006

OTHER PUBLICATIONS

J Zhou, F Zeng, X Gao, S Xie, S Wei. "Preparation of Arsenic Trioxide Albumin Microspheres and its Release Characteristics in Vitro." Journal of Huazhong University of Science and Technology. vol. 25 No. 3, 2005, pp. 310-312.*
LSC Wan, PWS Heng, LW Chan. "Drug Encapsulation in Alginate Microspheres by Emulsification." Journal of Microencapsulation, vol. 9 No. 3, 1992, pp. 309-316.*
JD Rule, EN Brown, NR Sottos, SR White, JS Moore. "Wax Protected Catalyst Microspheres for Efficient Self-Healing Materials." Advanced Materials, vol. 17 No. 2, 2005, pp. 205-208.*
T Mogues, J Li, J Coburn, Dj Kuter. "IgG antibodies against bovine serum albumin in humans—their prevalence and response to exposure to bovine serum albumin." Journal of Immunological Methods, vol. 300, 2005, pp. 1-11.*
Medical Journal of the Chinese People's Armed Police Forces, vol. 15 No. 01 Jan. 2004; http//www.cnki.net; 1994-2007 China Academic Journal Electronic Publishing House. Arsenic trioxide induces apoptosis in HUVECs and inhibits angiogenesis in CAM. 3 pages (No Translation Available).
Journal of Shandong University (Health Sciences) vol. 40 No. 2; Apr. 2002; hppt//www.cnki.net; 1994-2008 China Academic Journal Electronic Publishing House. Comparative study on the effects of arsenic trioxide and cisplatin on the ovarian carcinoma cell strain 3 AO in vitro. 3 pages (No Translation Available).
Journal of Practical Oncology; vol. 21 No. 1, 2006; hppt//www.cnki.net; 1994-2007 China Academic Journal Electronic Publishing House. 4 pages (No Translation Available).
Chin J. Radiat Oncol. Mar. 2003, vol. 12 No. 1; hppt//www.cnki.net; 1994-2008 China Academic Journal Electronic Publishing House. Radiation enhancement and induced apoptosis in ovarian cancer cells by arsenic trioxide. 4 pages (No Translation Available).
Journal of Experimental Hematology, 2002; 10 (1): 35-39; The Expression of FA s, Fa sL and Bcl-2 on RMA Cells during the Process of Apoptosis Induced by Chemotherapeutic Drugs; hppt//www.cnki.net; 1994-2007 China Academic Journal Electronic Publishing House. 5 pages (No Translation Available).
J. Fujian Med Univ. Jun. 2003 vol. 37 No. 2; hppt//www.cnki.net; 1994-2008 China Academic Journal Electronic Publishing House. 3 pages (No Translation Available).
Chin. J. Oncol. May 2003, vol. 25 No. 3; hppt//www.cnki.net; 1994-2007 China Academic Journal Electronic Publishing House. 1 page (No Translation Available).
Effects of Arsenic Trioxide by Transcatheter Arterial Chemoembolization on Rabbits with Hepatic Vx-2 Carcinoma; hppt//www.cnki.net; 1994-2008 China Academic Journal Electronic Publishing House. 3 pages (No Translation Available).
Chin. J. Postgrad Med. Jun. 2006, vol. 29 No. 6B; hppt//www.cnki.net; 1994-2007 China Academic Journal Electronic Publishing House. 3 pages (No Translation Available).

(Continued)

*Primary Examiner* — Frederick Krass
*Assistant Examiner* — Isaac Shomer
(74) *Attorney, Agent, or Firm* — Thomas, Kayden, Horstemeyer & Risley, LLP

(57) ABSTRACT

The present disclosure relates to a kind of sodium alginate microsphere vascular embolus that contains water-soluble drug and preparation and application thereof. The embolus preparation falls into dry microsphere type and wet one that are made of degradable materials. The drug carrier can be sodium alginate, human serum albumin, chitosan or sodium hyalurate, solidifying and forming microsphere together with calcium ion solution under presence of static charge. The microsphere can have a diameter in the range of 20-1000 μm and can be divided into a wide variety of sizes in case of need. The present disclosure adopts raw materials that are good at mechanical strength, bio-compatibility, bio-degradability and stability. In vitro experiments, animal trials and clinical observations reveal that this embolus is a good targeting medication for embolism treatment and immunochemotherapy, which is safe, effective for the treatment of solid tumors including primary liver cancer, lung cancer, renal tumors, bladder cancer, uterine cancer, ovary cancer, colon carcinoma and rectal cancer.

13 Claims, No Drawings

OTHER PUBLICATIONS

Chin. J. Surg., Jan. 2005, vol. 43 No. 1; hppt//www.cnki.net; 1994-2007 China Academic Journal Electronic Publishing House. The effect and mechanism of arsenic trioxide on hepatocellular carcinoma. 4 pages (No Translation Available).

* cited by examiner

SODIUM ALGINATE MICROSPHERE VASCULAR EMBOLUS CONTAINING WATER-SOLUBLE DRUG AND PREPARATION AND APPLICATION THEREOF

FIELD

The present disclosure relates a sodium alginate microsphere vascular embolus that contains water-soluble drug and preparation and application thereof. The embolus preparation falls into a dry microsphere type and a wet one that are made of degradable materials. The drug carrier can be sodium alginate, human serum albumin, chitosan or sodium hyalurate, solidifying and forming microsphere together with a calcium ion solution under presence of static charge. The microsphere has a diameter of 20 μm-1000 μm and can be divided into a wide variety of sizes in case of need. The present disclosure adopts raw materials that are good at bio-compatibility and bio-degradability. In vitro experiments, animal trials and clinical observations reveal that this embolus is a good targeting medication for embolism treatment and immunochemotherapy and is safe and effective for the treatment of solid tumors including primary liver cancer, lung cancer, renal tumors, bladder cancer, uterine cancer, ovary cancer, colon carcinoma and rectal cancer.

BACKGROUND

Arsenic trioxide ($As_2O_3$) is a main ingredient in Pishuang, a traditional Chinese medicine. The Chinese people began to use arsenic-containing medication to treat a wide variety of diseases as early as 2400 years ago. In early 1970s, scholars in Harbin Medical University tried to treat leukemia using Ailing-I injection solution. In August 1996 Science headlined Old Drug New Application highlighting effectiveness of $As_2O_3$ in treating acute promyelocytic leukemia used by Chinese physicians. From then on, arsenic-containing preparations became one of the hot spots in research on tumor treatment. Biological characteristics of arsenic-containing preparations fall into two aspects. On one hand, arsenic is a highly toxic material building up in body, combining with thiol proteins, affecting important enzyme system, undermining cell metabolism and inducing tumors. However, arsenic itself is not a carcinogen. On the other hand, arsenic is extensively distributed in nature while residing also in human body with a total amount of 14-21 mg, acting as an indispensable element. Certain amount of arsenic is able to stimulate hemopoiesis and promote cell growth. Arsenic-containing preparations enjoy many advantages in treating leukemia without inhibition of bone marrow, causing DIC, severe infection or bleeding. In addition, these preparations are able to penetrate blood-brain barrier very effective in fighting against solid tumors such as primary liver cancer, boasting merits including highly selective for tumor cells and little side and toxic effects.

Researches conducted by experts, both home and abroad, reveal that $As_2O_3$ can significantly inhibit solid tumors including liver cancer, stomach cancer, pancreas cancer, esophagus cancer, colon cancer, lung cancer, Ehrlich Ascites cancer, neuroblastoma, cervical carcinoma, ovary cancer and breast cancer. Domestic research institutes have reported safety and effectiveness of $As_2O_3$ in treating APL. Currently, American researchers are conducting a multi-centered research on APL trying to probe safety and effectiveness of $As_2O_3$ in treatment of APL. In 1999 the SDA approved $As_2O_3$ a National Class II new drug, formally produced and marketed by Harbin Yida Pharmaceuticals. In September 2000, the FDA also approved American Cell Therapeutic Company to produce and market $As_2O_3$ injection acting as a second-line drug for treatment of recurrent APL. At present, many research institutes, both home and abroad, are conducting clinical trials on treating multiple myeloma, malignant lymphoma, MDS and other malignant tumors.

Researches reveal that $As_2O_3$ takes effects as followings:

(1) Arsenic-containing preparations are cytotoxic (protoplasmic poison) inhibiting cell propagation, suppressing nuclear acid metabolism in tumor cells, interfering synthesis of DNA and RNA, halting protein synthesis, blocking mitosis of cells thus killing tumor cells;

(2) Arsenic-containing preparations are able to induce apoptosis. They combine thiol-base (—SH) containing materials, affecting trans-membrane potential of mitochondria, down regulating ratio of Bcl-2/Bax, and activating apoptosis effectors molecule caspase 3, 8, Fas and Fas-L, and increasing free $Ca^{2+}$ in the cells;

(3) Arsenic-containing preparations can induce cell differentiation. In anti-leukemia researches these preparations presented effect on inducing maturation and differentiation of promyelocyte, however, their effect on solid is still unreported; and (4) Arsenic-containing preparations help induce apoptosis of endothelial cells of blood vessels and inhibit angiogenesis. Yu Zhiyong et al. (Arsenic trioxide induces apoptosis in HUVECs and inhibits angiogenesis in CAM, Medical Journal of the Chinese People's Armed Police Forces, 2004(1)) conducted researches on $As_2O_3$'s effect on inducing apoptosis and inhibiting angiogenesis of endothelial cells of blood vessels of human umbilical vein, revealing $As_2O_3$ is able to inhibit growth of HUVECs, induce cell apoptosis and inhibit angiogenesis.

Huang Shouguo et al. (Comparative study on the effects of arsenic trioxide and cisplatin on the ovarian carcinoma cell strain 3AO in vitro, Acta Academiae Medicinae Shandong, 2002(2)) compared effect of $As_2O_3$ with Cisplatin onto human ovary cancer strain 3AO, revealing that $As_2O_3$ is able to block S phase and induce typical apoptosis in morphology. Compared with cDDP, $As_2O_3$ is more effective in inhibiting growth, inducing apoptosis and blocking S phase of 3AO. Wei Guoqing et al. (Journal of Practical Oncology, 2006(1)) conducted experiments probing effect of a combination of daunorubicin (DNR), Ara-C, Homoharringtonine (H) and vincristine (VCR) onto in vitro cytotoxicity of acute non-APL (ANPL), revealing that $As_2O_3$ is free from cross drug resistance with Ara-C, Homoharringtonine and VCR, but partly has cross drug resistance with DNR. Thus $As_2O_3$ can be used to form a new chemotherapy cohort with DNR and/or VCR treating naive or recurrent ANPL. Zhang Daxi et al. (Radiation enhancement and induced apoptosis in ovarian cancer cells by arsenic trioxide, Chinese Journal of Radiation Oncology, 2003(1)) probed effect of a combination of $As_2O_3$ with radiation therapy onto human ovary cancer cell strain SKOV3, finding that $As_2O_3$ within normal clinical dosage range can enhance effect of the radiation therapy in routine graded dosages.

Zhu Hongli et al. (The Expression of Fas, FasL and Bcl-2 on RMA Cells during the Process of Apoptosis Induced by Chemotherapeutic Drugs, Journal of Experimental Hematology, 2002(1)) probed effect of a combination of chemotherapeutic VP 16, $As_2O_3$, ATRA with cytokines IL2, IL6 and GM CSF onto apoptosis of mouse T lymphoma, finding the combination is able to induce apoptosis with lower drug concentration and ahead time of apoptosis, showing a synergistic effect, and providing experimental data for treatment of malignant lymphoma using chemotherapeutic cohort. Su Ying et al. (Effect of Arsenic Trioxide Combined with Interferon in K562 and K562/ADM Cell Lines, Journal of Fujian Medical University, 2003(2)) studied effect of a combination of $As_2O_3$ and interferon onto drug-resistance cell strains K562 and K562/ADM, indicating $As_2O_3$ is able to inhibit expression of Bcl-2 protein of K562 and K562/ADM, induce apoptosis and the effect has a dosage-time effect. A cohort of IFN α-2b and $As_2O_3$ is able to enhance effect onto K562, however less effective to enhance effect onto K562/ADM, indicating $As_2O_3$ is able to inhibit K562 and K562/ADM's expression of GST-πand Bcl-2 proteins and induce apoptosis, however futile to expression of P-gp protein. IFN α-2b can enhance the above effect. Song Tiefang et al. (Chinese Journal of Oncology, 2003(3)) conducted researches on inhibitive effect of a combination of $As_2O_3$ with TNF onto human liver cancer cell strain HepG2, revealing $As_2O_3$ and TNF are synergistic each other, and the combination is more effective than any individual in the combination in inducing apoptosis.

Currently, most arsenic-containing medications are administered via non-intestinal routes, including in vein injection, in muscle injection, local injection, in cavity administration, drug-pump administration and intervention administration. Zheng Mingyou et al. (Effects of Arsenic Trioxide by Transcatheter Arterial Chemoembolization on Rabbits with Hepatic Vx-2 Carcinoma, Cancer Research On Prevention and Treatment, 2004(12)) probed inhibition to rabbit Vx2 hepatic transplantation carcinoma of $As_2O_3$ via hepatic artery catheter perfusion, revealing it is significantly effective in treating tumors showing a dose dependent relation, and $As_2O_3$ induces apoptosis via up regulating expression of bax gene. Qi Xiaojun et al. (Chinese Journal of Postgraduates of Medicine, 2006(17)) studied effect of a combination of injection of $As_2O_3$ via B-ultrasound-guided percutaneous puncture with via-hepatic-artery chemotherapy embolism onto liver suffering from primary cancer, finding the combination is superior to using via-hepatic-artery chemotherapy embolism exclusively. Zhu Anlong et al. (The effect and mechanism of arsenic trioxide on hepatocellular carcinoma, Chinese Journal of Surgery, 2005(1)) studied chemotherapeutic value of $As_2O_3$ for primary liver cancer as well as its best administration route. They punctured 17 patients unsuitable for surgical operation via femoral artery or axillary artery, identifying location and range of the tumors by using hepatic arteriography DSA. They imbedded perfusion devices (micro-pump) under skin for left, right and proper hepatic artery, linking the micro-pump to a micro-injector. The pump-injected $As_2O_3$ was administered to the cancerous areas for consecutive five days at a dosage of 20 mg/d. After having undergone 4 therapeutic courses, 6 cancerous lesions shrank the size by 50% plus and no new lesions occurred (PR=35.2%); and 8 lesions shrank by 10-49% (overall effectiveness rate was 41.1%), one lesion did not change, and 2 lesions boomed by 25% plus. No explicit side effects took place. The results indicate that administration of $As_2O_3$ to local lesions is effective for solid tumors enjoying advantages such little side effects and explicit effect.

Commonly seen side effects include digestive reactions such as dry mouth, bitter mouth, fullness of abdomen, skin itching and rash, rarely seen side effects include urinary reactions such as edema in face and lower limbs and loss of leukocytes. Disorders in blood coagulation are rare. Further researches are needed for the best dosage, combination and therapeutic course of use of $As_2O_3$. Other issues should also be clarified such as kinds of solid tumors besides APL that are sensitive to $As_2O_3$, safety of $As_2O_3$, whether or not it will cause secondary tumor, induce drug resistance and problems caused by combination with other drugs, etc.

The therapy method of arterial embolism is to inject embolus to micro-arteries causing mechanical blocking and inhibiting tumor growth. In 1981 Kato debuted this therapy method combining chemotherapeutic drugs with embolism materials treating malignant tumors unsuitable for surgical operations. In recent years this method has been applied to treat liver cancer, renal cancer, tumors in pelvis and head and neck showing effective result. However, this method suffers from a high relapse rate.

Microsphere preparations are particles with a diameter of 20-1000 μm that contain certain drugs and are made with proper auxiliary materials. Effectiveness of microsphere for embolism purpose depends on diameter, degrading speed of skeleton of the microsphere, drug-carrying speed and drug release speed. The drug-containing microsphere preparations can block micro-vessels that supply blood to the cancerous lesions releasing anti-tumor drugs and killing cancerous cells, enabling the drugs to be targeted and controllable. This kind of method for drug administration is able to improve drug distribution in vivo and pharmacokinetic features, increase bioavailability of drugs, improving treatment effect and alleviate toxic or side effects.

Microsphere preparations for arterial embolism should have characteristics as the followings: powerful enough to embolism, strong mechanically and stable physically and chemically, the drug can be released slowly and persistently, maintaining a therapeutic concentration in the targeted areas; the drug carrier can be eroded by the receiver, and is biocompatible, free from antigenicity, and free from harms to body even lingering around the targeted areas for a long time.

Thus some topics for this research subject includes: how to prepare microsphere embolus containing $As_2O_3$ by using degradable materials, how to apply the microsphere embolus to treatment of tumors locally, how to prevent $As_2O_3$ encapsulated by degradable materials from leaking, and how to prevent wet microsphere that is water soluble from leaking.

Microsphere preparations are made with certain drugs and auxiliary materials using micro-encapsulation technology. Administration of drugs in the form of microsphere helps the drugs to be site targeted and release controllable, this kind of method for drug administration is able to improve drug distribution in vivo and pharmacokinetic features, increase bioavailability of drugs, improving treatment effect and alleviate toxic or side effects. Chemotherapeutic-drug-containing Microspheres via arterial embolism can cluster in arterial vessels around the lesion blocking blood supply to the lesion and releasing drug persistently, effectively inducing apoptosis and causing ischemic and anoxia and death of cancerous cells. Currently the most frequently used microsphere preparation is with $As_2O_3$, which can increase its concentration immediately after in vein administration, spreading to tissues around the tumor lesion causing side effects including digestive symptoms, peripheral neuritis, dry skin and pigmentation, even renal impairment, pleural collection and ascites. To overcome the shortcomings, the present disclosure creates the sodium alginate microsphere vascular embolus containing water-soluble drug, enabling some special carriers to encapsulate water-soluble drugs using some special physical and chemical processes. In addition, the microsphere preparations will be administered locally or via intervention route reducing drug dosage, alleviating side effects and improving therapeutic effect.

SUMMARY

One objective of the present disclosure is to provide a kind of sodium alginate microsphere vascular embolus that contains water-soluble drug.

Another objective of the present disclosure is to provide a method for preparing sodium alginate microsphere vascular embolus that contains water-soluble drug.

Another objective of the present disclosure is to provide two medicament forms that store the embolus in the form of dry microsphere and wet microsphere.

Yet another objective of the present disclosure is to provide application approaches of the embolus for embolism and immunochemotherapy of malignant solid tumors including primary liver cancer, lung cancer, renal tumors, stomach cancer, bladder cancer, uterine cancer, ovary cancer, colon carcinoma and rectal cancer.

The present disclosure achieves its goals using technology as described below:

A sodium alginate microsphere vascular embolus that contains water-soluble drug, wherein the embolus contains compound drug carrier and water-soluble drug, the drug carrier containing the said water-soluble drug.

A technological resolution, wherein the ratio of weight of the compound drug carrier to the weight of the said water-soluble drug can be in the range of 3:1 to 30:1.

A technological resolution, wherein the water-soluble drug can be arsenic trioxide, amycin, daunorubicin, mitomycin, fluorouracil, Cisplatin, cyclophosphamide, vincaleucoblastine, or vincristine.

A technological resolution, wherein the compound drug carrier can be a mixture liquid containing sodium alginate, human serum albumin, and chitosan, or a blend of sodium alginate, human serum albumin, and sodium hyalurate. The weight ratio between sodium alginate, human serum albumin, and chitosan/sodium hyalurate can be in the range of 1:1:0.1 to 1:10:0.9.

A technological resolution, wherein the said embolus is round or ovary micro-gel-bead or microsphere that is stored in bivalent-metal-cation solidifying liquid.

A technological resolution, wherein the bivalent-metal-cation solidifying liquid is calcium chloride or barium chloride solidifying solution.

A technological resolution, wherein the micro-gel-bead or microsphere has a diameter that can be in the range of 20-1000 μm.

A technological resolution, wherein the said embolus preparation is powder-like particles.

A technological resolution, wherein the said powder-like particle has a diameter that can be in the range of 10-800 μm.

A method for preparing a sodium alginate microsphere vascular embolus that contains water-soluble drug, wherein the preparation procedures are as below:

(1) Weighing the water-soluble drugs according to the proportion and dissolve the drugs using certain solvents obtaining water-soluble drug solution;

(2) Weighing sodium alginate, human serum albumin, and chitosan/sodium hyalurate with a weight ratio in the range of 1:1:0.1 to 1:10:0.9, dissolving the above materials, obtaining solutions of sodium alginate, human serum albumin, and chitosan/sodium hyalurate respectively;

(3) Preparing calcium chloride solution or barium chloride solution using water, obtaining solidifying solutions with a concentration in the range of 1-20%;

(4) Mixing the water-soluble drug solution obtained in step (1) with the human serum albumin solution obtained in step (2), and adding sodium alginate, chitosan or sodium hyalurate solutions one by one, and dripping the mixture liquid through a high-pressure-static-charge microsphere-generation device into the solidifying solution forming round or ovary microsphere or micro-gel-bead;

(5) Draining out the solidifying solution from step (4) from the round or ovary microsphere or micro-gel-bead obtaining microsphere or micro-gel-bead that is made of sodium alginate and contains water-soluble drugs;

(6) Mixing acetone and the solidifying solution obtained from step (3) with a proportion ratio in the range of 1:0.5-100, obtaining enhanced solidifying solution. Pouring the enhanced solidifying solution into the microsphere or micro-gel-bead solution obtained from step (5), allowing to stand for 3 min to 30 min; and (7) Draining out the enhanced solidifying solution obtained from step (6), washing out at least two times using the solidifying solution obtained from step (3), pouring a certain amount of fluid wax or iodipin acting as preservation solution. Keeping the microsphere or micro-gel-bead soaked in the preservation solution and subpackage the final product sodium alginate microsphere vascular embolus that contains water-soluble drug.

A technological resolution, wherein the high-pressure-static-charge microsphere-generation device in said step (5) is a static charge generation instrument, which has positive and negative poles. The positive pole is connected with needle of a micro-injection device, and the negative pole is linked to a stainless ring soaked in the solidifying solution. The injection device contains a mixture of water-soluble drugs, sodium alginate, human serum albumin, chitosan or sodium hyalurate. The mixture is dripped into the solidifying solution forming microsphere.

A technological resolution, wherein the preparation procedures are as below: take 1-5 portions of suspension of sodium alginate microsphere or micro-gel-bead containing water-soluble drugs, 1-3 portions of water, 10-30 portions of 5-25% mannitol, freeze the mixture in a low temperature refrigerator for at least 2 hours, then place the frozen mixture into a freezing drier for 15-48 hours, obtaining powder-like particle.

Application of a targeting embolus preparation to arterial embolism and immunochemotherapy of primary liver cancer, lung cancer, renal tumors, uterine cancer, ovary cancer, stomach cancer, bladder cancer, colon carcinoma and rectal cancer.

DETAILED DESCRIPTION

Clinical application: Guided by interventional ultrasound or interventional radiation, insert catheter into an artery that supplies blood to the target organ conducing arteriography, on which depend to select diameter of microsphere for embolism. The embolism procedures should be conducted using micro-catheter as much as possible and sterile operations should be obeyed. Uncap the bottle and allow to stand for settlement, inspire the preservation solution (solidifying solution) in the bottle using a syringe and add equal portion of normal saline solution to rinse the microsphere for three times, or inspire the solidifying solution in the bottle using a syringe and add equal portion of normal saline solution, and transfer the mixture to a sterile bowel, rinse the microspheres with 50-60 ml of normal saline solution once, and add certain amount of diluted contrast medium and mix even (enabling microsphere to sufficiently suspend in the contrast medium). Under fluoroscopy guide, irrigate the mixture slowly, or in several portions (precautions to over much embolism), until the contrast medium significantly lowers its speed completing embolism. Repeat the arteriography determining embolism effect.

In case the embolus preparation is in the form of powder-like particle, solve the dry microsphere contained in sealed containers using normal saline solution (wet microsphere), and add certain amount of diluted contrast medium and mix even (enabling microsphere to sufficiently suspend in the contrast medium). Under fluoroscopy guide, irrigate the mixture slowly, or in several portions (precautions to over much embolism), until the contrast medium significantly lowers its speed completing embolism. Repeat the arteriography determining embolism effect.

In one embodiment, among others, the sodium alginate acting as drug carrier is a natural extract collected from natural plant brown alga. The sodium alginate is a sodium polysaccharide that contains β-D-mannitol and α-L-gulose. It is a linear macromolecule that has a molecular weight in the range of 50,000-200,000 Dalton, very powerful in combining water, forming a sticky gel when solved in water. Under presence of calcium ion, its macromolecular chains can cross link and solidify being able to be processed as round or ovary wet or solid microsphere with different sizes. This kind of microsphere is good at biocompatibility. In the body of creatures, calcium ions seep out and the microspheres degrade without causing debris and toxic effect within 3-6 months in the form of falling out of chains. The microspheres can cause perpetual embolism (when the embolus stays in the blood vessel as long as 2 months, thrombosis in blood vessels of patients take place perpetually blocking the blood vessels) of blood vessels of targeting organs achieving therapeutic goals.

In practical operation, the "biologically multifunction microspheres" physically block small arteries supplying blood to the tumors or arteries around the tissues cutting off blood supply and nutrient supply causing ischemia, anoxia, atrophy and necrosis. Dwindling blood supply to targeted organs also facilitates surgical operations. As an anti-tumor drug carrier, the microspheres can slowly release drugs to specific site on specific time, significantly improving therapeutic effect, alleviating side or toxic effects of the drugs, and taking effects of both embolism and chemotherapy.

One embodiment, among others, uses some water-soluble drugs to treat cancers and applies semi-cross-link structure and degradability of the microsphere, considering empirical usage of embolus made of bio-degradable materials, and the advantages such as high safety, free from toxicity, free from antigenicity, free from genetic toxicity, free from reproductive toxicity and free from carcinogenicity. Usage of bio-degradable materials acting as drug carrier to carry anti-tumor drugs can help send drugs to specific site on specific time, killing tumor cells and achieving therapy goal.

One embodiment firstly mixes the water-soluble drug with human serum albumin, facilitating absorption of the former by the latter, and adds sodium alginate solution and chitosan solution or sodium hyalurate forming a mixture solution. Then drip the mixture liquid through a high-pressure-static-charge microsphere-generation device into the above mentioned solidifying solution forming round or ovary microsphere or micro-gel-bead. Mixture of odium alginate solution and chitosan solution or sodium hyalurate can increase density of the network structure of drug carrier baffling drug release, overcoming the conundrum that a single carrier is unable to encapsulate water-soluble drugs.

Mix the water-soluble drug with sodium alginate, human serum albumin and chitosan, or with sodium alginate, human serum albumin and sodium hyalurate, then drip the mixture liquid through a high-pressure-static-charge microsphere-generation device into the above mentioned solidifying solution forming round or ovary microsphere or micro-gel-bead. The water-soluble drugs can be absorbed by the human serum albumin.

In order to enhance solidification of the wet microsphere or wet micro-gel-bead, a special organic solvent acetone is used to better encapsulate the microsphere in company with well adjusted concentration, frequency and speed. Owing to this solidification enhancement, the microspheres become even, smooth and contain well dispersed drugs. Active groups in the drugs can be well protected by the microsphere carriers keeping stable in vivo preventing water-soluble drugs from leaking over fast or early, achieving clinical goals.

One embodiment relates to microsphere vascular embolus that contains water-soluble drug and made by bio-degradable materials, having advantages such as large load of drugs, long lingering time in vivo and highly specific for certain targets, becoming the most promising targeting release-controllable drug system. The microsphere carries a certain amount of cations on its surface causing the microspheres repulsive for each other. In real usage, the user should select dosage depending on status of the lesion choosing interventional radiation or surgical intubation. After inserting the catheter to an artery of the target organ and conducting arteriography, the user should mix the microsphere and contrast medium using a syringe, and slowly inject the mixture without causing coagulation and blocking in the catheter.

The present disclosure can be further described by the following embodiments, which is used in a descriptive sense only and not for purpose of limitation.

EXAMPLE 1

Preparation of Sodium Alginate Microsphere that Contains $As_2O_3$, Human Serum Albumin, and Chitosan.

1. Preliminary procedures before encapsulation
   Treatment of glassware: Let glassware that has been washed clean dry naturally, then place them in a high temperature baking oven for heating for 3 h at 300° C. (removal of bacteria and pyrogens).
2. Preparation of $As_2O_3$ and human serum albumin
   Transfer accurately weighed 700 mg of market available $As_2O_3$ to glassware, drip water for injection use for solvency; dissolve 1000 mg of human serum albumin using water for injection use, obtaining a mixture of $As_2O_3$ and human serum albumin.
3. Preparation of sodium alginate
   Transfer accurately weighed 1 g of market available sodium alginate to glassware, add normal saline solution with stirring until the sodium alginate is fully dissolved obtaining a sodium alginate solution.
4. Prepare a 7% calcium chloride solution.
5. Dissolve 100 mg of chitosan using water for injection use, obtaining a 0.2 wt % chitosan solution.
6. Mix above prepared mixture of $As_2O_3$ and human serum albumin, and mixture of chitosan and sodium alginate, obtaining another mixture.
7. Inspire the mixture obtained from step 6 using a disposable sterile syringe, drip the mixture through a high-pressure static-charge microsphere generation device into the above-mentioned calcium chloride solution, obtaining sodium alginate microsphere or micro-gel-bead that contains $As_2O_3$, which settles on bottom of the container. The particle size of the microsphere can be in the range of 100-300 μm.
8. Mix acetone and the solidifying solution obtained from step 4 with a proportion ratio of 1:0.5, obtaining an enhanced solidifying solution. Pour the enhanced solidifying solution into the microsphere or micro-gel-bead solution obtained from step 7 that contains $As_2O_3$-containing sodium alginate microsphere or micro-gel-bead, allow to stand for 3 min to 30 min.
9. Drain out the enhanced solidifying solution obtained from step 8, wash out at least two times using solidifying solution obtained from step 4, pour certain amount of fluid wax acting as preservation solution. Keep the microsphere or micro-gel-bead soaked in the preservation solution and subpackage the final product sodium alginate micro-gel-bead or microsphere mixture that contains $As_2O_3$.
10. Freeze dry process of the microsphere: take 1 portion of suspension of sodium alginate microsphere containing $As_2O_3$ from step 9, 1 portion of water, 10 portions of mannitol, freeze the mixture in a low temperature refrigerator for at least 2 hours, then place the frozen mixture into a freezing drier for 15 hours, obtaining a powder-like particle.
11. Drain out supernatant of the container and transfer micro-gel-bead on the bottom to a baking oven for drying, seal and store. The powder-like particles can have a diameter in the range of 75-150 μm. Before use, soak the dry microspheres using normal saline solution for several minutes to restore wet microspheres. Alternatively, drain out supernatant and rinse using water for two times and use immediately.

EXAMPLE 2

Preparation of Sodium Alginate Microsphere that Contains Amycin, Human Serum Albumin, and Sodium Hyalurate.

1. Preliminary procedures before encapsulation

Treatment of Glassware:

Let glassware that have been washed clean dry naturally, place them in a high temperature baking oven for heating for 3 h at 300° C. (removal of bacteria and pyrogens).

2. Preparation of amycin and human serum albumin.

Transfer accurately weighed 700 mg of market available amycin to glassware, drip water for injection use for solvency; solve 10 g of human serum albumin using water for injection use, obtaining a mixture of amycin and human serum albumin.

3. Preparation of sodium alginate:

Transfer accurately weighed 10 g of market available sodium alginate to glassware, add normal saline solution with stirring until sodium alginate is fully dissolved obtaining a sodium alginate solution.

4. Prepare a 7% barium chloride solution.
5. Dissolve 1 g of sodium hyalurate using water for injection use obtaining a 0.2 wt % sodium hyalurate solution.
6. Mix the above prepared mixture of amycin and human serum albumin, and mixture of sodium hyalurate and sodium alginate, obtaining another mixture.
7. Inspire mixture obtained from step 6 using a disposable sterile syringe, drip the mixture through a high-pressure static-charge microsphere generation device into the above-mentioned calcium chloride solution, obtaining sodium alginate microsphere or micro-gel-bead that contains amycin, which settles on bottom of the container. The particle size of the microsphere can be in the range of 150-450 μm.
8. Mix acetone and the solidifying solution obtained from step 4 with a proportion ratio of 1:100, obtaining an enhanced solidifying solution. Pour the enhanced solidifying solution into the microsphere or micro-gel-bead solution obtained from step 7 that contains amycin-containing sodium alginate microsphere or micro-gel-bead, allow to stand for 3 min to 30 min.
9. Drain out the enhanced solidifying solution obtained from step 8, wash out at least two times using solidifying solution obtained from step 4, pour certain amount of iodipin acting as preservation solution. Keep the microsphere or micro-gel-bead soaked in the preservation solution and subpackage the final product sodium alginate micro-gel-bead or microsphere mixture that contains amycin.
10. Freeze dry process of the microsphere: take 5 portions of suspension of sodium alginate microsphere containing amycin from step 9, 3 portions of water, 30 portions of mannitol, freeze the mixture in a low temperature refrigerator for at 12 hours, then place the frozen mixture into a freezing drier for 48 hours, obtaining powder-like particle.
11. Drain out supernatant of the container and transfer micro-gel-bead on the bottom to a baking oven for drying, seal and store. The powder-like particle can have a diameter in the range of 100-250 μm. Before use, soak the dry microsphere using normal saline solution for several minutes restoring wet microsphere. Alternatively, drain out supernatant and rinse using water for two times and use immediately.

EXAMPLE 3

Preparation of Sodium Alginate Microsphere that Contains DNR, Human Serum Albumin, and Chitosan.

1. Preliminary procedures before encapsulation

Treatment of Glassware:

Let glassware that have been washed clean dry naturally, place them in a high temperature baking oven for heating for 3 h at 300° C. (removal of bacteria and pyrogens).

2. Preparation of DNR and human serum albumin

Transfer accurately weighed 700 mg of market available DNR to glassware, drip water for injection use for solvency; dissolve 1000 mg of human serum albumin using water for injection use, obtaining a mixture of DNR and human serum albumin.

3. Preparation of sodium alginate:

Transfer accurately weighed 1 g of market available sodium alginate to glassware, add normal saline solution with stirring until sodium alginate is fully dissolved, obtaining a sodium alginate solution.

4. Prepare a 7% calcium chloride solution.
5. Dissolve 100 mg of chitosan using water for injection use, obtaining a 0.2 wt % chitosan solution.
6. Mix above prepared mixture of DNR and human serum albumin, and mixture of chitosan and sodium alginate, obtaining another mixture.
7. Inspire mixture obtained from step 6 using a disposable sterile syringe, drip the mixture through a high-pressure static-charge microsphere generation device into the above-mentioned calcium chloride solution, obtaining sodium alginate microsphere or micro-gel-bead that contains DNR, which settles on bottom of the container. The particle size of the microsphere can be in the range of 300-500 μm.
8. Mix acetone and the solidifying solution obtained from step 4 with a proportion ratio of 1:10, obtaining an enhanced solidifying solution. Pour the enhanced solidifying solution into the microsphere or micro-gel-bead solution obtained from step 7 that contains DNR-containing sodium alginate microsphere or micro-gel-bead, allow to stand for 3 min to 30 min.
9. Drain out the enhanced solidifying solution obtained from step 8, wash out at least two times using solidifying solution obtained from step 4, pour a certain amount of fluid wax acting as preservation solution. Keep the microsphere or micro-gel-bead soaked in the preservation solution and subpackage the final product sodium alginate micro-gel-bead or microsphere mixture that contains DNR.
10. Freeze dry process of the microsphere: take 1 portion of suspension of sodium alginate microsphere containing DNR from step 9, 3 portions of water, 20 portions of mannitol, freeze the mixture in a low temperature refrigerator for 12 hours, then place the frozen mixture into a freezing drier for 48 hours, obtaining powder-like particle.
11. Drain out supernatant of the container and transfer micro-gel-bead on the bottom to a baking oven for drying, seal and store. The powder-like particle can have a diameter in the range of 150-350 μm. Before use, soak the dry microsphere using normal saline solution for several minutes restoring wet microsphere. Alternatively, drain out supernatant and rinse using water for two times and use immediately.

EXAMPLE 4

Preparation of Sodium Alginate Microsphere that Contains Mitomycin, Human Serum Albumin, and Sodium Hyalurate.

1. Preliminary procedures before encapsulation
Treatment of glassware:
Let glassware that have been washed clean dry naturally, place them in a high temperature baking oven for heating for 3 h at 300° C. (removal of bacteria and pyrogens).
2. Preparation of mitomycin and human serum albumin
Transfer accurately weighed 70 mg of market available mitomycin to glassware, drip water for injection use for solvency; dissolve 1 g of human serum albumin using water for injection use, obtaining a mixture of mitomycin and human serum albumin.
3. Preparation of sodium alginate:
Transfer accurately weighed 1 g of market available sodium alginate to glassware, add normal saline solution with stirring until sodium alginate is fully dissolved obtaining a sodium alginate solution.
4. Prepare a 7% barium chloride solution.
5. Dissolve 100 mg of sodium hyalurate using water for injection use, obtaining a 0.2 wt % sodium hyalurate solution.
6. Mix above prepared mixture of mitomycin and human serum albumin, and mixture of sodium hyalurate and sodium alginate, obtaining another mixture.
7. Inspire mixture obtained from step 6 using a disposable sterile syringe, drip the mixture through a high-pressure static-charge microsphere generation device into the above-mentioned calcium chloride solution, obtaining sodium alginate microsphere or micro-gel-bead that contains mitomycin, which settles on bottom of the container. The particle size of the microsphere can be in the range of 20-50 μm.
8. Mix acetone and the solidifying solution obtained from step 4 with a proportion ratio of 1:100, obtaining an enhanced solidifying solution. Pour the enhanced solidifying solution into the microsphere or micro-gel-bead solution obtained from step 7 that contains mitomycin-containing sodium alginate microsphere or micro-gel-bead, allow to stand for 3 min to 30 min.
9. Drain out the enhanced solidifying solution obtained from step 8, wash out at least two times using solidifying solution obtained from step 4, pour a certain amount of iodipin acting as preservation solution. Keep the microsphere or micro-gel-bead soaked in the preservation solution and subpackage the final product sodium alginate micro-gel-bead and microsphere mixture that contains mitomycin.
10. Freeze dry process of the microsphere: take 5 portions of suspension of sodium alginate microsphere containing mitomycin from step 9, 3 portions of water, 30 portions of mannitol, freeze the mixture in a low temperature refrigerator for at 12 hours, then place the frozen mixture into a freezing drier for 48 hours, obtaining powder-like particle.
11. Drain out supernatant of the container and transfer micro-gel-bead on the bottom to a baking oven for drying, seal and store. The powder-like particle can have a diameter in the range of 10-35 μm. Before use, soak the dry microsphere using normal saline solution for several minutes restoring wet microsphere. Alternatively, drain out supernatant and rinse using water for two times and use immediately.

EXAMPLE 5

Preparation of Sodium Alginate Microsphere that Contains Fluorouracil, Human Serum Albumin, and Chitosan 1. Preliminary procedures before encapsulation
Treatment of glassware:
Let glassware that have been washed clean dry naturally, place them in a high temperature baking oven for heating for 3 h at 300° C. (removal of bacteria and pyrogens).
2. Preparation of fluorouracil and human serum albumin
Transfer accurately weighed 700 mg of market available fluorouracil to glassware, drip water for injection use for solvency; dissolve 1000 mg of human serum albumin using water for injection use, obtaining a mixture of fluorouracil and human serum albumin.
3. Preparation of sodium alginate:
Transfer accurately weighed 1 g of market available sodium alginate to glassware, add normal saline solution with stirring until sodium alginate is fully dissolved obtaining sodium alginate solution.
4. Prepare a 7% calcium chloride solution.
5. Dissolve 100 mg of chitosan using water for injection use, obtaining a 0.2 wt % chitosan solution.
6. Mix above prepared mixture of fluorouracil and human serum albumin, and mixture of chitosan and sodium alginate, obtaining another mixture.
7. Inspire mixture obtained from step 6 using a disposable sterile syringe, drip the mixture through a high-pressure static-charge microsphere generation device into the above-mentioned calcium chloride solution, obtaining sodium alginate microsphere or micro-gel-bead that contains fluorouracil, which settles on bottom of the container. The particle size of the microsphere can be in the range of 500-700 μm.
8. Mix acetone and the solidifying solution obtained from step 4 with a proportion ratio of 1:0.5, obtaining enhanced solidifying solution. Pour the enhanced solidifying solution into the microsphere or micro-gel-bead solution obtained from step 7 that contains fluorouracil-containing sodium alginate microsphere or micro-gel-bead, allow to stand for 3 min to 30 min.
9. Drain out the enhanced solidifying solution obtained from step 8, wash out at least two times using solidifying solution obtained from step 4, pour a certain amount of fluid wax acting as preservation solution. Keep the microsphere or micro-gel-bead soaked in the preservation solution and subpackage the final product sodium alginate micro-gel-bead or microsphere mixture that contains fluorouracil.
10. Freezing dry process of the microsphere: take 1 portion of suspension of sodium alginate microsphere containing fluorouracil from step 9, 1 portion of water, 10 portions of mannitol, freeze the mixture in a low temperature refrigerator for at 2 hours, then place the frozen mixture into a freezing drier for 25 hours, obtaining powder-like particle.
11. Drain out supernatant of the container and transfer micro-gel-bead on the bottom to a baking oven for drying, seal and store. The powder-like particle can have a diameter in the range of 350-500 μm. Before use, soak the dry microsphere using normal saline solution for several minutes restoring wet microsphere. Alternatively, drain out supernatant and rinse using water for two times and use immediately.

EXAMPLE 6

Preparation of Sodium Alginate Microsphere that Contains Cisplatin, Human Serum Albumin, and Chitosan 1. Preliminary procedures before encapsulation
Treatment of glassware:
Let glassware that have been washed clean dry naturally, place them in a high temperature baking oven for heating for 3 h at 300° C. (removal of bacteria and pyrogens).
2. Preparation of cisplatin and human serum albumin
Transfer accurately weighed 700 mg of market available cisplatin to glassware, drip water for injection use for solvency; dissolve 1000 mg of human serum albumin using water for injection use, obtaining a mixture of cisplatin and human serum albumin.
3. Preparation of sodium alginate:
Transfer accurately weighed 1 g of market available sodium alginate to glassware, add normal saline solution with stirring until sodium alginate is fully dissolved obtaining sodium alginate solution.
4. Prepare a 7% calcium chloride solution.
5. Dissolve 100 mg of chitosan using water for injection use, obtaining a 0.2 wt % chitosan solution.
6. Mix above prepared mixture of cisplatin and human serum albumin, and mixture of chitosan and sodium alginate, obtaining another mixture.
7. Inspire mixture obtained from step 6 using a disposable sterile syringe, drip the mixture through a high-pressure static-charge microsphere generation device into the above-mentioned calcium chloride solution, obtaining sodium alginate microsphere or micro-gel-bead that contains cisplatin, which settles on bottom of the container. The particle size of the microsphere can be in the range of 700-900 μm.
8. Mix acetone and the solidifying solution obtained from step 4 with a proportion ratio of 1:0.5, obtaining enhanced solidifying solution. Pour the enhanced solidifying solution into the microsphere or micro-gel-bead solution obtained from step 7 that contains cisplatin-containing sodium alginate microsphere or micro-gel-bead, allow to stand for 3 min to 30 min.
9. Drain out the enhanced solidifying solution obtained from step 8, wash out at least two times using solidifying solution obtained from step 4, pour a certain amount of fluid wax acting as preservation solution. Keep the microsphere or micro-gel-bead soaked in the preservation solution and subpackage the final product sodium alginate micro-gel-bead or microsphere mixture that contains cisplatin.
10. Freezing dry process of the microsphere: take 1 portion of suspension of sodium alginate microsphere containing cisplatin from step 9, 1 portion of water, 10 portions of mannitol, freeze the mixture in a low temperature refrigerator for at 10 hours, then place the frozen mixture into a freezing drier for 48 hours, obtaining powder-like particle.
11. Drain out supernatant of the container and transfer micro-gel-bead on the bottom to a baking oven for drying, seal and store. The powder-like particle can have a diameter in the range of 500-700 μm. Before use, soak the dry microsphere using normal saline solution for several minutes restoring wet microsphere. Alternatively, drain out supernatant and rinse using water for two times and use immediately.

EXAMPLE 7

Preparation of Sodium Alginate Microsphere that Contains Cyclophosphamide, Human Serum Albumin, and Chitosan 1. Preliminary procedures before encapsulation
Treatment of glassware:
Let glassware that have been washed clean dry naturally, place them in a high temperature baking oven for heating for 3 h at 300° C. (removal of bacteria and pyrogens).
2. Preparation of cyclophosphamide and human serum albumin
Transfer accurately weighed 700 mg of market available cyclophosphamide to glassware, drip water for injection use for solvency; dissolve 1000 mg of human serum albumin using water for injection use, obtaining a mixture of cyclophosphamide and human serum albumin.
3. Preparation of sodium alginate:
Transfer accurately weighed 1 g of market available sodium alginate to glassware, add normal saline solution with stirring until sodium alginate is fully dissolved, obtaining a sodium alginate solution.
4. Prepare a 7% calcium chloride solution.
5. Dissolve 100 mg of chitosan using water for injection use, obtaining a 0.2 wt % chitosan solution.
6. Mix above prepared mixture of cyclophosphamide and human serum albumin, and mixture of chitosan and sodium alginate, obtaining another mixture.
7. Inspire mixture obtained from step 6 using a disposable sterile syringe, drip the mixture through a high-pressure static-charge microsphere generation device into the above-mentioned calcium chloride solution, obtaining sodium alginate microsphere or micro-gel-bead that contains cyclophosphamide, which settles on bottom of the container. The particle size of the microsphere can be in the range of 800-1000 μm.
8. Mix acetone and the solidifying solution obtained from step 4 with a proportion ratio of 1:0.5, obtaining enhanced solidifying solution. Pour the enhanced solidifying solution into the microsphere or micro-gel-bead solution obtained from step 7 that contains cyclophosphamide-containing sodium alginate microsphere or micro-gel-bead, allow to stand for 3 min to 30 min;
9. Drain out the enhanced solidifying solution obtained from step 8, wash out at least two times using solidifying solution obtained from step 4, pour certain amount of fluid wax acting as preservation solution. Keep the microsphere or micro-gel-bead soaked in the preservation solution and subpackage the final product sodium alginate micro-gel-bead microsphere mixture that contains cyclophosphamide.
10. Freeze dry process of the microsphere: take 1 portion of suspension of sodium alginate microsphere containing cyclophosphamide from step 9, 1 portion of water, 10 portions of mannitol, freeze the mixture in a low temperature refrigerator for at 10 hours, then place the frozen mixture into a freezing drier for 48 hours, obtaining powder-like particle.
11. Drain out supernatant of the container and transfer micro-gel-bead on the bottom to a baking oven for drying, seal and store. The powder-like particle can have a diameter in the range of 600-750 μm. Before use, soak the dry microsphere using normal saline solution for several minutes restoring wet microsphere. Alternatively, drain out supernatant and rinse using water for two times and use immediately.

EXAMPLE 8

Preparation of Sodium Alginate Microsphere that Contains Vincaleucoblastine, Human Serum Albumin, and Chitosan 1. Preliminary procedures before encapsulation
Treatment of glassware:
Let glassware that have been washed clean dry naturally, place them in a high temperature baking oven for heating for 3 h at 300° C. (removal of bacteria and pyrogens).
2. Preparation of vincaleucoblastine and human serum albumin
Transfer accurately weighed 700 mg of market available vincaleucoblastine to glassware, drip water for injection use for solvency; dissolve 1000 mg of human serum albumin using water for injection use, obtaining a mixture of vincaleucoblastine and human serum albumin.
3. Preparation of sodium alginate:
Transfer accurately weighed 1 g of market available sodium alginate to glassware, add normal saline solution with stirring until sodium alginate is fully dissolved, obtaining a sodium alginate solution.
4. Prepare a 7% calcium chloride solution.
5. Dissolve 100 mg of chitosan using water for injection use, obtaining a 0.2 wt % chitosan solution.
6. Mix above prepared mixture of vincaleucoblastine and human serum albumin, and mixture of chitosan and sodium alginate, obtaining another mixture.
7. Inspire mixture obtained from step 6 using a disposable sterile syringe, drip the mixture through a high-pressure static-charge microsphere generation device into the above-mentioned calcium chloride solution, obtaining sodium alginate microsphere or micro-gel-bead that contains vincaleucoblastine, which settles on bottom of the container. The particle size of the microsphere can be in the range of 300-500 μm.
8. Mix acetone and the solidifying solution obtained from step 4 with a proportion ratio of 1:0.5, obtaining an enhanced solidifying solution. Pour the enhanced solidifying solution into the microsphere or micro-gel-bead solution obtained from step 7 that contains vincaleucoblastine-containing sodium alginate microsphere or micro-gel-bead, allow to stand for 3 min to 30 min.
9. Drain out the enhanced solidifying solution obtained from step 8, wash out at least two times using solidifying solution obtained from step 4, pour certain amount of fluid wax acting as preservation solution. Keep the microsphere or micro-gel-bead soaked in the preservation solution and subpackage the final product sodium alginate micro-gel-bead or microsphere mixture that contains vincaleucoblastine.
10. Freeze dry process of the microsphere: take 1 portion of suspension of sodium alginate microsphere containing vincaleucoblastine from step 9, 1 portion of water, 10 portions of mannitol, freeze the mixture in a low temperature refrigerator for at 10 hours, then place the frozen mixture into a freezing drier for 48 hours, obtaining powder-like particle.
11. Drain out supernatant of the container and transfer micro-gel-bead on the bottom to a baking oven for drying, seal and store. The powder-like particle can have a diameter in the range of 150-250 μm. Before use, soak the dry microsphere using normal saline solution for several minutes restoring wet microsphere. Alternatively, drain out supernatant and rinse using water for two times and use immediately.

EXAMPLE 9

Preparation of Sodium Alginate Microsphere that Contains Vincristine, Human Serum Albumin, and Chitosan 1. Preliminary procedures before encapsulation
Treatment of glassware:
Let glassware that have been washed clean dry naturally, place them in a high temperature baking oven for heating for 3 h at 300° C. (removal of bacteria and pyrogens).
2. Preparation of vincristine and human serum albumin
Transfer accurately weighed 700 mg of market available vincristine to glassware, drip water for injection use for solvency; dissolve 1000 mg of human serum albumin using water for injection use, obtaining a mixture of vincristine and human serum albumin.
3. Preparation of sodium alginate:
Transfer accurately weighed 1 g of market available sodium alginate to glassware, add normal saline solution with stirring until sodium alginate is fully dissolved, obtaining a sodium alginate solution.
4. Prepare a 7% calcium chloride solution.
5. Dissolve 100 mg of chitosan using water for injection use, obtaining a 0.2 wt % chitosan solution.
6. Mix above prepared mixture of vincristine and human serum albumin, and mixture of chitosan and sodium alginate, obtaining another mixture.
7. Inspire mixture obtained from step 6 using a disposable sterile syringe, drip the mixture through a high-pressure static-charge microsphere generation device into the above-mentioned calcium chloride solution, obtaining sodium alginate microsphere or micro-gel-bead that contains vincristine, which settles on bottom of the container. The particle size of the microsphere can be in the range of 300-500 μm.
8. Mix acetone and the solidifying solution obtained from step 4 with a proportion ratio of 1:0.5, obtaining an enhanced solidifying solution. Pour the enhanced solidifying solution into the microsphere or micro-gel-bead solution obtained from step 7 that contains vincristine-containing sodium alginate microsphere or micro-gel-bead, allow to stand for 3 min to 30 min.
9. Drain out the enhanced solidifying solution obtained from step 8, wash out at least two times using solidifying solution obtained from step 4, pour a certain amount of fluid wax acting as preservation solution. Keep the microsphere or micro-gel-bead soaked in the preservation solution and subpackage the final product sodium alginate micro-gel-bead microsphere that contains vincristine.
10. Freeze dry process of the microsphere: take 1 portion of suspension of sodium alginate microsphere containing vincristine from step 9, 1 portion of water, 10 portions of mannitol, freeze the mixture in a low temperature refrigerator for at 10 hours, then place the frozen mixture into a freezing drier for 48 hours, obtaining powder-like particle.
11. Drain out supernatant of the container and transfer micro-gel-bead on the bottom to a baking oven for drying, seal and store. The powder-like particle can have a diameter in the range of 150-250 μm. Before use, soak the dry microsphere using normal saline solution for several minutes restoring wet microsphere. Alternatively, drain out supernatant and rinse using water for two times and use immediately.

EXAMPLE 10

Preparation of Sodium Alginate Microsphere that Contains Camptothecin, Human Serum Albumin, and Chitosan 1. Preliminary procedures before encapsulation Treatment of glassware:

Let glassware that have been washed clean dry naturally, place them in a high temperature baking oven for heating for 3 h at 300° C. (removal of bacteria and pyrogens).

2. Preparation of camptothecin and human serum albumin

Transfer accurately weighed 700 mg of market available camptothecin to glassware, drip water for injection use for solvency; dissolve 1000 mg of human serum albumin using water for injection use, obtaining a mixture of camptothecin and human serum albumin.

3. Preparation of sodium alginate:

Transfer accurately weighed 1 g of market available sodium alginate to glassware, add normal saline solution with stirring until sodium alginate is fully dissolved, obtaining a sodium alginate solution.

4. Prepare a 7% calcium chloride solution.
5. Dissolve 100 mg of chitosan using water for injection use, obtaining a 0.2 wt % chitosan solution.
6. Mix above prepared mixture of camptothecin and human serum albumin, and mixture of chitosan and sodium alginate, obtaining another mixture.
7. Inspire mixture obtained from step 6 using a disposable sterile syringe, drip the mixture through a high-pressure static-charge microsphere generation device into the above-mentioned calcium chloride solution, obtaining sodium alginate microsphere or micro-gel-bead that contains camptothecin, which settles on bottom of the container. The particle size of the microsphere can be in the range of 300-500 μm.
8. Mix acetone and the solidifying solution obtained from step 4 with a proportion ratio of 1:0.5, obtaining an enhanced solidifying solution. Pour the enhanced solidifying solution into the microsphere or micro-gel-bead solution obtained from step 7 that contains camptothecin-containing sodium alginate microsphere or micro-gel-bead, allow to stand for 3 min to 30 min.

9 Drain out the enhanced solidifying solution obtained from step 8, wash out at least two times using solidifying solution obtained from step 4, pour a certain amount of fluid wax acting as preservation solution. Keep the microsphere or micro-gel-bead soaked in the preservation solution and subpackage the final product sodium alginate micro-gel-bead or microsphere mixture that contains camptothecin.

10. Freeze dry process of the microsphere: take 1 portion of suspension of sodium alginate microsphere containing camptothecin, 1 portion of water, 10 portions of mannitol, freeze the mixture in a low temperature refrigerator for at 12 hours, then place the frozen mixture into a freezing drier for 48 hours, obtaining powder-like particle.
11. Drain out supernatant of the container and transfer micro-gel-bead on the bottom to a baking oven for drying, seal and store. The powder-like particle can have a diameter in the range of 150-250 μm. Before use, soak the dry microsphere using normal saline solution for several minutes restoring wet microsphere. Alternatively, drain out supernatant and rinse using water for two times and use immediately.

Trial Example 1

Application of Sodium Alginate Microsphere Vascular Embolus Containing As2O3

1. Establishment and usage of rabbit model of liver cancer: 50 purely blooded clean New Zealand rabbits (provided by Beijing Center for Experiment-use Animals), uneven in genders, aged 3-4 months, body weight 2-3 kg.
2. Materials: Rabbits having subcutaneous Vx2 transplantation carcinoma are provided by Ultrasound Bioengineering Institute of Beijing Medical University. Bcl2, bax immunohistochemistry stain kits are bought from Bossed, and VEGF immunohistochemistry stain kits are bought from NeoMarker. DAB developing kits and slide gluing agents are bought from Maxim, and catheter for hepatic artery catheter perfusion are bought from BD company.
3. Experimental method 1: slice fish-like tissue into masses measuring 1-2 $mm^3$. The tissues should be rampantly growing part on the edge of the lesion of Vx2 transplantation carcinoma. Plant the masses into left anterior lobe of liver. Two weeks later a cancerous lesion with a diameter 1 cm and grows in the form of infiltration takes place. At this time, puncture and insert and fix the intubation on the root of hepatic artery. The animals are randomized into 5 groups (10 animals in each group) using random digit table method: negative control group (receiving normal saline solution), positive control group (receiving cisplatin 1.28 mg/kg·d), experiment group 1 ($As_2O_3$ 0.6 mg/kg·d), experiment group 2 ($As_2O_3$ 1.2 mg/kg·d) and experiment group 3 ($As_2O_3$ 1.96 mg/kg·d). Administer the rabbits drugs obtained from the Example 1 for consecutive 7 days. Five weeks later after planting the cancerous mass, cut normal hepatic tissue near the tumor and full cancerous tissue, weighing tumor weight, take one slide for both optical microscopy and electron microscopy from the cancerous tissue (the same site as before planting, within 15 cm) and normal tissue respectively.
4. Experimental method 2: 30 purely blooded clean New Zealand rabbits (provided by Beijing Center for Experiment-use Animals), uneven in genders, aged 3-4 months, body weight 2-3 kg. The rabbits are randomized into 3 groups (10 rabbits in each group). Two weeks later after having established rabbit liver cancer model, insert catheter via right femoral artery into the hepatic artery administering drug to arteries that supply blood to the tumor. (a) Control group: irrigate 10 ml of normal saline solution via hepatic artery; (b) group receiving microsphere without containing drug: irrigate sodium alginate microsphere at a dosage of 5 mg/kg; (c) group receiving microsphere containing $As_2O_3$: irrigate microsphere that contains $As_2O_3$ at a dosage of 5 mg/kg. On the $21^{st}$ day scan liver using spiral CT and sacrifice the rabbits taking out liver and fixing using 10% formalin. Slice cancerous tissue at multiple sites and embed the specimen using wax, stain with HE, examine using microscope, and calculate tumor volume.

5. Observatory parameters:

Tumor weight and average rate for inhibition of tumor weight for the positive control group and experiment group: Average rate for inhibition of tumor weight=(1−average tumor weight of group receiving drug/average tumor weight of negative control group)×100%. Observation using transmission electron microscope: tumor cells, cell volume of hepatic cells, morphology of nuclear and changes of nuclear chromatin. Examination of expression of bcl 2 bax genes, and expression of VEGF, in which the stain result is used to determine standard expression of bcl 2 bax genes; cells whose plasma or membrane stained brown-yellow are determined positive cells. Positive cells <5% is judged (−), 5%-15% (+), 15%-50% (++), >50% (+++). As for determining expression of VEGF, when new-born endothelial cells of capillaries, part tumor cell plasma and/or membrane are stained brown, they are judged positive. The cells that are explicitly stained are VEGF positive and those inexplicitly stained or free from being stained are judged VEGF negative.

6. Statistic method: data collected are expressed in the form of X±s, and SAS 8.1 is used to conduct q test, Fisher's exact test.

Treatment of nude mouse loaded with human hepatocarcinoma using microsphere containing immunochemotherapeutic drug via arterial embolism.

Trial Example 2

Mode of Mouse Suffering from U14 Transplantation Cervical Cancer

1. Dilute U14 cervical cancer cells to $7\times10^6$ cancer cells/ml. Disinfect armpit area of right anterial lime of 34 NIH mice that weigh 18-22 g. Inject the dilute cancer cells subcutaneously at a dosage of 0.1 ml/each mouse ($7\times10^5$ cancer cells/each mouse). After the mice grow for 3-4 weeks with the cancer cells, remove the transplantation tumor mass slicing it dices measuring 1 mm×1 mm×1 mm, and again inoculate the dices under capsule of left lobe of liver of the mice.

2. Treatment of Hela-bearing nude mouse

Ten days later after having inoculated the tumor mass, open the original cut measuring longest and shortest diameter of lesion of the transplantation tumor under surgical microscope, as well as irrigate drug via intubation to hepatic artery. The animals are randomized into: (A) normal saline solution group; (B) IL-2 group; (C) IL-2 liposome group; (D) Exclusive chemotherapy group; (E) IL-2+chemotherapy; (F) IL-2 liposome group+chemotherapy group.

Two weeks later measure six animals of each group, obtaining the longest and shortest diameter of lesion of the transplantation tumor. Calculate tumor volume and compare tumor growth rate (in which tumor volume growth rate is quotient of dividing post-treatment tumor volume by pre-treatment tumor volume). Conduct HE stain to observe necrosis degree of the tumor (mild: 0-30%; moderate: 30-70%; severe: 71-100%), and to observe infiltration of lymphocytes, and natural survival time of naked rats after treatment.

Embolism of hepatic artery for rats suffering from transportation liver cancer

3. Establishment of rat transportation liver cancer model

Take 0.5-1 ml of cancerous ascites from abdomen of Wistar rats after they have been inoculated Walker-256 tumor cells for 3-5 days. Inject the ascites with sterile procedures under skin of healthy rats. 7-10 days later a tumor mass measuring 1-2 cm takes place. Take some fresh-like cancerous mass slicing it to dices as big as 1 mm³ and inoculating it to left lateral lobe of liver of rats. One week later liver cancer model that has a cancerous mass with a diameter of 0.5-1 cm takes place. Take 30 liver cancer model rats and irrigate embolus preparation via gastroduodenal and hepatic proper artery using PE-50 catheter under surgical microscope, owing to which the hepatic artery can be blocked. Together with irrigation of the drug transiently block common hepatic artery and right branch of proper hepatic artery. Having irrigated the drug, close the abdomen and raise the rats in the cages.

Trial examples 3-7: conduct trials the same as those in the examples 1-2 using sodium alginate embolus that contains amycin, daunorubicin, mitomycin, fluorouracil, Cisplatin, cyclophosphamide, vincaleucoblastine, vincristine or Camptothecin.

Clinical Application:

1. Guided by interventional ultrasound or interventional radiation, insert catheter into an artery that supplies blood to the target organ conducing arteriography, depending on which diameter of microsphere for embolism is selected. The embolus containing $As_2O_3$ that is obtained from the example 1 is for treatment patient suffering from primary liver cancer. The embolism procedures should be conducted using micro-catheter as much as possible and sterile operations should be obeyed. Uncap the bottle and allow to stand for settlement, inspire the preservation solution (solidifying solution) in the bottle using a syringe and add equal portion of normal saline solution to rinse the microsphere for three times, or inspire the preservation solution (solidifying solution) in the bottle using a syringe and add equal portion of normal saline solution, and transfer the mixture to a sterile bowel, rinse the microspheres with 50-60 ml of normal saline solution once, and add certain amount of diluted contrast medium and mix even (enabling microsphere to sufficiently suspend in the contrast medium). Under fluoroscopy guide, irrigate the mixture slowly, or in several portions (precautions to over much embolism), until the contrast medium significantly lowers its speed completing embolism. Repeat the arteriography determining embolism effect.

2. Guided by interventional ultrasound or interventional radiation, insert catheter into an artery that supplies blood to the target organ conducing arteriography, depending on which diameter of microsphere for embolism is selected. The embolus containing amycin that is obtained from the example 2 is for treatment patient suffering from lung cancer. The embolism procedures should be conducted using micro-catheter as much as possible and sterile operations should be obeyed. Uncap the bottle and allow to stand for settlement, inspire the preservation solution (solidifying solution) in the bottle using a syringe and add equal portion of normal saline solution to rinse the microsphere for three times, or inspire the preservation solution (solidifying solution) in the bottle using a syringe and add equal portion of normal saline solution, and transfer the mixture to a sterile bowel, rinse the microspheres with 50-60 ml of normal saline solution once, and add certain amount of diluted contrast medium and mix even (enabling microsphere to sufficiently suspend in the contrast medium). Under fluoroscopy guide, irrigate the mixture slowly, or in several portions (precautions to over much embolism), until the contrast medium significantly lowers its speed completing embolism. Repeat the arteriography determining embolism effect.

3. Guided by interventional ultrasound or interventional radiation, insert catheter into an artery that supplies blood to the target organ conducing arteriography, depending on which diameter of microsphere for embolism is selected. The embolus containing daunorubicin that is obtained from the example 3 is for treatment patient suffering from renal cancer. The embolism procedures should be conducted using micro-catheter as much as possible and sterile operations should be obeyed. Uncap the bottle and allow to stand for settlement, inspire the preservation solution (solidifying solution) in the bottle using a syringe and add equal portion of normal saline solution to rinse the microsphere for three times, or inspire the preservation solution (solidifying solution) in the bottle using a syringe and add equal portion of normal saline solution, and transfer the mixture to a sterile bowel, rinse the microspheres with 50-60 ml of normal saline solution once, and add certain amount of diluted contrast medium and mix even (enabling microsphere to sufficiently suspend in the contrast medium). Under fluoroscopy guide, irrigate the mixture slowly, or in several portions (precautions to over much embolism), until the contrast medium significantly lowers its speed completing embolism. Repeat the arteriography determining embolism effect.

4. Guided by interventional ultrasound or interventional radiation, insert catheter into an artery that supplies blood to the target organ conducing arteriography, depending on which diameter of microsphere for embolism is selected. The embolus containing $As_2O_3$ that is obtained from the example 1 is for treatment patient suffering from uterus cancer. The embolism procedures should be conducted using micro-catheter as much as possible and sterile operations should be obeyed. Uncap the bottle and allow to stand for settlement, inspire the preservation solution (solidifying solution) in the bottle using a syringe and add equal portion of normal saline solution to rinse the microsphere for three times, or inspire the preservation solution (solidifying solution) in the bottle using a syringe and add equal portion of normal saline solution, and transfer the mixture to a sterile bowel, rinse the microspheres with 50-60 ml of normal saline solution once, and add certain amount of diluted contrast medium and mix even (enabling microsphere to sufficiently suspend in the contrast medium). Under fluoroscopy guide, irrigate the mixture slowly, or in several portions (precautions to over much embolism), until the contrast medium significantly lowers its speed completing embolism. Repeat the arteriography determining embolism effect.

5. Guided by interventional ultrasound or interventional radiation, insert catheter into an artery that supplies blood to the target organ conducing arteriography, depending on which diameter of microsphere for embolism is selected. The embolus containing $As_2O_3$ that is obtained from the example 1 is for treatment patient suffering from ovary cancer. The embolism procedures should be conducted using micro-catheter as much as possible and sterile operations should be obeyed. Uncap the bottle and allow to stand for settlement, inspire the solidifying solution in the bottle using a syringe and add equal portion of normal saline solution to rinse the microsphere for three times, or inspire the solidifying solution in the bottle using a syringe and add equal portion of normal saline solution, and transfer the mixture to a sterile bowel, rinse the microspheres with 50-60 ml of normal saline solution once, and add certain amount of diluted contrast medium and mix even (enabling microsphere to sufficiently suspend in the contrast medium). Under fluoroscopy guide, irrigate the mixture slowly, or in several portions (precautions to over much embolism), until the contrast medium significantly lowers its speed completing embolism. Repeat the arteriography determining embolism effect.

6. Guided by interventional ultrasound or interventional radiation, insert catheter into an artery that supplies blood to the target organ conducing arteriography, depending on which diameter of microsphere for embolism is selected. The embolus containing $As_2O_3$ that is obtained from the example 1 is for treatment patient suffering from stomach cancer. The embolism procedures should be conducted using micro-catheter as much as possible and sterile operations should be obeyed. Uncap the bottle and allow to stand for settlement, inspire the preservation solution (solidifying solution) in the bottle using a syringe and add equal portion of normal saline solution to rinse the microsphere for three times, or inspire the preservation solution (solidifying solution) in the bottle using a syringe and add equal portion of normal saline solution, and transfer the mixture to a sterile bowel, rinse the microspheres with 50-60 ml of normal saline solution once, and add certain amount of diluted contrast medium and mix even (enabling microsphere to sufficiently suspend in the contrast medium). Under fluoroscopy guide, irrigate the mixture slowly, or in several portions (precautions to over much embolism), until the contrast medium significantly lowers its speed completing embolism. Repeat the arteriography determining embolism effect.

7. Guided by interventional ultrasound or interventional radiation, insert catheter into an artery that supplies blood to the target organ conducing arteriography, depending on which diameter of microsphere for embolism is selected. The embolus containing mitomycin that is obtained from the example 4 is for treatment patient suffering from bladder cancer. The embolism procedures should be conducted using micro-catheter as much as possible and sterile operations should be obeyed. Uncap the bottle and allow to stand for settlement, inspire the preservation solution (solidifying solution) in the bottle using a syringe and add equal portion of normal saline solution to rinse the microsphere for three times, or inspire the preservation solution (solidifying solution) in the bottle using a syringe and add equal portion of normal saline solution, and transfer the mixture to a sterile bowel, rinse the microspheres with 50-60 ml of normal saline solution once, and add certain amount of diluted contrast medium and mix even (enabling microsphere to sufficiently suspend in the contrast medium). Under fluoroscopy guide, irrigate the mixture slowly, or in several portions (precautions to over much embolism), until the contrast medium significantly lowers its speed completing embolism. Repeat the arteriography determining embolism effect.

8. Guided by interventional ultrasound or interventional radiation, insert catheter into an artery that supplies blood to the target organ conducing arteriography, depending on which diameter of microsphere for embolism is selected. The embolus containing mitomycin that is obtained from the example 4 is for treatment patient suffering from colon or rectal cancer. The embolism procedures should be conducted using micro-catheter as much as possible and sterile operations should be obeyed. Uncap the bottle and allow to stand for settlement, inspire the preservation solution (solidifying solution) in the bottle using a syringe and add equal portion of normal saline solution to rinse the microsphere for three times, or inspire the preservation solution (solidifying solution) in the bottle using a syringe and add equal portion of normal saline solution, and transfer the mixture to a sterile bowel, rinse the microspheres with 50-60 ml of normal saline solution once, and add certain amount of diluted contrast medium and mix even (enabling microsphere to sufficiently suspend in the contrast medium). Under fluoroscopy guide, irrigate the mixture slowly, or in several portions (precautions to over much embolism), until the contrast medium significantly lowers its speed completing embolism. Repeat the arteriography determining embolism effect.

We claim:

1. A method for preparing a sodium alginate microsphere vascular embolus containing a water-soluble drug, comprising the steps of:
    preparing a solution comprising a water-soluble drug wherein the water-soluble drug is $As_2O_3$;
    preparing a solution comprising sodium alginate;
    preparing a solution comprising human serum albumin;
    preparing a solution comprising a chemical selected from the group consisting of chitosan and sodium hyalurate;
    preparing a solidifying solution;
    mixing said water-soluble drug solution with said sodium alginate solution, said human serum albumin solution, and said chemical solution;
    dripping said mixture through a high-pressure-static-charge microsphere-generation device into said solidifying solution; and
    obtaining a sodium alginate microsphere vascular embolus from said solidifying solution.

2. The method of claim 1, wherein the step of preparing a solution comprising water-soluble drug further comprises:
    weighing a quantity of said water-soluble drug; and
    dissolving said quantity of water-soluble drug using a solvent.

3. The method of claim 1, wherein the step of preparing a solution comprising sodium alginate further comprises:
    weighing a quantity of said sodium alginate; and
    dissolving said quantity of sodium alginate using a solvent.

4. The method of claim 1, wherein the step of preparing a solution comprising said chemical further comprises:
    weighing a quantity of said chemical; and
    dissolving said quantity of chemical using a solvent.

5. The method of claim 1, wherein the weight ratio of said sodium alginate, said human serum albumin, and said chemical is in the range of 1:1:0.1 to 1:10:0.9.

6. The method of claim 1, wherein said solidifying solution comprises barium chloride with a concentration in the range of 1 to 20%.

7. The method of claim 1, wherein said solidifying solution is a calcium chloride solution with a concentration in the range of 1 to 20%.

8. The method of claim 7, wherein the step of obtaining a sodium alginate microsphere vascular embolus further comprises the steps of:
    draining out said solidifying solution;
    soaking said sodium alginate microsphere vascular embolus in an enhanced solidifying solution;
    draining out said enhanced solidifying solution; and
    washing said sodium alginate microsphere vascular embolus with said solidifying solution.

9. The method of claim 8, wherein said enhanced solidifying solution comprises acetone and said solidifying solution with a proportion ratio in the range of 1:0.5-100.

10. The method of claim 8, wherein said sodium alginate microsphere vascular embolus soaks in said enhanced solidifying solution for a period in the range of 3 min to 30 min.

11. The method of claim 8, further comprising the step of washing said sodium alginate microsphere vascular embolus with a preservation solution.

12. The method of claim 1, wherein said high-pressure-static-charge microsphere-generation device is a static charge generation instrument having positive and negative poles, said positive pole connected with a needle of a micro-injection device, and said negative pole linked to a stainless ring soaked in the solidifying solution, said micro-injection device including said mixture.

13. A method for preparing a sodium alginate microsphere vascular embolus containing a water-soluble drug, comprising the steps of:
    preparing a solution comprising $As_2O_3$;
    preparing a solution comprising sodium alginate;
    preparing a solution comprising human serum albumin;
    preparing a solution comprising a chemical selected from the group consisting of chitosan and sodium hyalurate;
    preparing a solidifying solution of barium chloride or calcium chloride with a concentration in the range of 1 to 20%;
    mixing said $As_2O_3$ solution with said sodium alginate solution, said human serum albumin solution, and said chemical solution, wherein the weight ratio of said sodium alginate, said human serum albumin, and said chemical is in the range of 1:1:0.1 to 1:10:0.9;
    dripping said mixture through a high-pressure-static-charge microsphere-generation device into said solidifying solution, wherein said high-pressure-static-charge microsphere-generation device is a static charge generation instrument having positive and negative poles, said positive pole connected with a needle of a micro-injection device, and said negative pole linked to a stainless ring soaked in the solidifying solution, said micro-injection device including said mixture, thereby obtaining a sodium alginate microsphere vascular embolus from said solidifying solution, wherein the step of obtaining a sodium alginate microsphere vascular embolus further comprises the steps of:
    draining out said solidifying solution;
    soaking said sodium alginate microsphere vascular embolus in an enhanced solidifying solution comprising acetone and said solidifying solution with a proportion ratio in the range of 1:0.5-100 for a period in the range of 3 min to 30 min;
    draining out said enhanced solidifying solution; and
    washing said sodium alginate microsphere vascular embolus with said solidifying solution and optionally with a preservation solution.

* * * * *